United States Patent [19]

Hakomori et al.

[11] Patent Number: 5,230,900
[45] Date of Patent: Jul. 27, 1993

[54] ANTIBODY-MEDIATED AND LIGAND-MEDIATED TARGETING OF DIFFERENTIATION-INDUCERS TO TUMOR CELLS

[75] Inventors: Sen-itiroh Hakomori, Mercer Island; Michiro Otaka; Anil Singhal, both of Seattle, all of Wash.

[73] Assignee: The Biomembrane Institute, Seattle, Wash.

[21] Appl. No.: 730,513

[22] Filed: Jul. 12, 1991

Related U.S. Application Data

[63] Continuation of Ser. No. 214,261, Jul. 1, 1988, abandoned.

[51] Int. Cl.$^5$ .......................... A61K 37/22; A61K 9/66
[52] U.S. Cl. ...................................... 424/450; 424/85.8; 514/21; 436/829
[58] Field of Search .................... 424/450, 9, 497, 501, 424/489, 85.8; 514/21; 436/829

[56] References Cited

U.S. PATENT DOCUMENTS

| | | | |
|---|---|---|---|
| 4,372,949 | 2/1983 | Kodama et al. | 424/450 X |
| 4,460,560 | 7/1984 | Tökes et al. | 424/497 X |
| 4,501,728 | 2/1985 | Geho et al. | 428/402.2 X |
| 4,552,812 | 11/1985 | Margel et al. | 424/497 X |
| 4,674,480 | 6/1987 | Lemelson | 424/9 X |
| 4,764,359 | 8/1988 | Lemelson | 424/9 X |
| 4,806,466 | 2/1989 | Papahadjopoulos et al. | 436/829 X |
| 4,837,028 | 6/1989 | Allen | 424/450 |
| 4,855,090 | 8/1989 | Wallach | 424/450 X |
| 4,920,016 | 4/1980 | Allen et al. | 424/450 |
| 5,064,823 | 11/1991 | Lee et al. | 514/198 |

FOREIGN PATENT DOCUMENTS

| | | | |
|---|---|---|---|
| 36277 | 9/1981 | European Pat. Off. | 424/450 |
| WO91/05806 | 5/1991 | PCT Int'l Appl. | |

OTHER PUBLICATIONS

Kapil Mehta et al, "Induction of Tissue Transglutaminase in Human Peripheral Blood Monocytes by Intracellular Delivery of Retinoids", Journal of Leukocyte Biology, 41:341–348 (1987).

The Merck Index, 10th Ed., (Merck & Co., Inc., Rayway, N.J., 1983) p. 1057.

Otaka et al., "Antibody-Mediated Targeting of Differentiation Inducers to Tumor Cells: Inhibition of Colonic Cancer Cell Growth In Vitro and In Vivo", Biochemical and Biophysical Research Communications, vol. 158, No. 1, Jan. 16, 1989, pp. 202–208.

Primary Examiner—Robert L. Stoll
Assistant Examiner—Daniel S. Metzmaier
Attorney, Agent, or Firm—Sughrue, Mion, Zinn, Macpeak & Seas

[57] ABSTRACT

The present invention relates to compositions which mediate antibody and ligand targeting of differentiation-inducers to tumor cells and methods for employing the same.

6 Claims, 3 Drawing Sheets

FIG. 2C LIPOSOME ACCUMULATION IN LIVERS

FIG. 2D LIPOSOME ACCUMULATION IN SPLEENS

FIG. 2E LIPOSOME ACCUMULATION IN LUNGS

FIG. 3 HT-29 TUMOR WEIGHT

FIG. 4 HRT-18 TUMOR WEIGHT

ANTIBODY-MEDIATED AND LIGAND-MEDIATED TARGETING OF DIFFERENTIATION-INDUCERS TO TUMOR CELLS

This is a continuation of application Ser. No. 07/214,261 filed 1 Jul. 1988, now abandoned.

FIELD OF THE INVENTION

The present invention relates to compositions which mediate antibody and ligand targeting of differentiation-inducers to tumor cells and methods for employing the same.

BACKGROUND OF THE INVENTION

Anti-tumor toxins and cytotoxic drugs have been targeted to tumor cells by directly coupling them to tumor-associated antibodies via a covalent linkage (Gregoriadis, G. et al, *Targeting of Drugs With Synthetic Systems*, Plenum Press, New York (1986)).

In addition, anti-tumor toxins and cytotoxic drugs have been targeted to tumor cells by indirectly coupling them to tumor-associated antibodies via microspheres (*Microspheres and Drug Therapy*, Eds. Davis. S. S. et al, Elsevier, New York (1984)). Microspheres are synthetic or natural particles (such as liposomes) having a diameter of up to at least 1.0 μm and include nanospheres which have a diameter of 10 to 100 nm.

However, there are major drawbacks to the above-discussed approaches to the direct and indirect coupling of anti-tumor toxins and cytotoxic drugs to tumor-associated antibodies. More specifically, antibody-toxin conjugates and antibody-cytotoxic drug conjugates arising from direct or indirect coupling are taken up rapidly by macrophages. Kupfer cells and other reticuloendothelial system cells before they can reach the tumor. As a result, less than 1% of the conjugates may actually reach the tumor. In addition, when antibody specificity is not restricted to tumor cells. i.e., if the target antigen is also expressed by a variety of normal cells, the conjugates are not only targeted to tumor cells but are also targeted to normal cells. Thus, since the anti-tumor toxins or cytotoxic drugs which are conventionally coupled to antibodies are highly toxic to normal cells as well as to tumor cells, they cause serious functional damage to normal cell systems, particularly to macrophages and other reticuloendothelial system cells. As a result, while a specific anti-tumor effect is observed in vitro using these conjugates, such a specific anti-tumor effect is less efficiently observed in vivo (Kao, Y. et al. *Biochim. Biophys. Acta*, 677:453–461 (1981); and Kirby, C. et al. *Life Sci.*, 27:2223–2230 (1980)).

Differentiation-inducers have been observed, in vitro, to change the phenotype of tumor cells so that it is similar to that of non-tumorigenic cells, i.e., to induce "contact inhibitability", low cell saturation density, contact orientation, inability to form colonies in soft agar, etc. (Patt, L. M. et al, Nature, 273:379–381 (1978): Tsao, D. et al. *Cancer Res.*, 42:1052–1058 (1982): Kim, Y. S. et al, *Gann Monogr. Cancer Res.*, 29:93–103 (1983): Sugimura, T. et al, *Gann Monogr. Cancer Res.*, 29:3–15 (1983): Prashad, N. et al, *Cancer Res.*, 47:2417–2424 (1987); and Reuben. L. et al, *Int. J. Cancer*, 40:224–229 (1987)). However, to date, no study has attempted to similarly alter tumorigenicity or malignancy in vivo. The concentration of differentiation-inducers required to effect the change in the phenotype of tumor cells in vitro is extremely low and not cytotoxic to normal cells. It is more difficult to employ differentiation-inducers in vivo because the necessary systemic concentration of unbound differentiation-inducer can be toxic to specific organs. Thus, to date, there has been no successful application of differentiation-inducers to convert the malignant phenotype to the normal cell phenotype in vivo.

Furthermore, to date, no study has been published or carried out on the targeting of differentiation-inducers via antibodies or any specific ligand directed to tumor cells, either in vitro or in vivo. This is a striking contrast to a number of studies which have been carried out on the targeting of anti-tumor toxins and cytotoxic drugs to tumor cells via antibodies or specific ligands directed to tumor cells. In addition, no study to date has been carried out to ascertain the most efficient way to target differentiation-inducers to tumor cells, either in vitro or in vivo.

SUMMARY OF THE INVENTION

Accordingly, an object of the present invention is to provide compositions useful for efficiently and specifically targeting differentiation-inducers via tumor-associated antibodies or ligands.

Another object of the present invention is to provide a method whereby differentiation-inducers can be efficiently and specifically targeted to tumor cells via tumor-associated antibodies or ligands so as to effectively treat the tumor cells.

These and other objects of the present invention will be apparent from the detailed description of the invention provided hereinafter.

In one embodiment, the above-described objects of the present invention have been met by a tumor-associated antibody or ligand conjugated to a synthetic or natural microsphere, preferably a ganglioside liposome, wherein said microsphere contains a differentiation-inducer therein.

In a further embodiment, the above-described objects of the present invention have been met by a method for treating a tumor comprising administering to a subject afflicted with a tumor, a pharmaceutically effective amount of a tumor-associated antibody or ligand conjugated to a synthetic or natural microsphere, preferably a ganglioside liposome, wherein said microsphere contains a differentiation-inducer therein.

In still another embodiment, the above-described objects of the present invention have been met by a tumor-associated antibody or ligand conjugated to a differentiation-inducer.

In a still further embodiment, the above-described objects of the present invention have been met by a method for treating a tumor comprising administering to a subject afflicted with a tumor, a pharmaceutically acceptable amount of a tumor-associated antibody or ligand conjugated to a differentiation-inducer.

DETAILED DESCRIPTION OF THE INVENTION

As discussed above, in one embodiment, the above-described objects of the present invention have been met by a tumor-associated antibody or ligand coupled to a synthetic or natural microsphere, preferably a ganglioside liposome, wherein said microsphere contains a differentiation-inducer therein.

The differentiation-inducer can be specifically targeted to tumor cells in vivo by means of the tumor-associated antibody or ligand. As a result, reduction or elimination of the malignant potential of the tumor cells can be achieved. That is, the conjugates of the present invention show a differentiation-inducing effect on tumor cells thereby causing conversion of the tumor cells into normal cells. Further, when targeted to normal cells, the conjugates of the present invention have no effect thereon and thus adverse side-effects are avoided. In addition, the gangliosides in the ganglioside liposomes are believed to prevent the conjugates of the present invention from interacting with macrophages or the reticuloendothelial system. Thus, a high proportion of the conjugates of the present invention can be specifically targeted to the tumor cells.

The particular synthetic microsphere employed in the present invention is not critical thereto. Examples of such synthetic microspheres include those formed from lactide glycolide copolymers, polyacrolein graft copolymers; carboxymethyl dextran, polylactide and polystyrene (*Microspheres and Drug Therapy*, Eds. Davis. S. S. et al, Elsevier, New York (1984)).

The above-described copolymers can be employed alone or in combination in the synthetic microspheres of the present invention.

The particular natural microspheres. i.e., liposomes employed in the present invention is not critical thereto. Ganglioside liposomes are preferred.

As used herein, the expression "ganglioside liposome" means a lipid bilayer containing gangliosides.

The primary liposome component constituting the lipid bilayer employed in the present invention is a phospholipid. The particular phospholipid employed in the present invention is not critical thereto. Examples of such phospholipids include dipalmitoyl phosphatidylcholine, distearyl phosphatidylcholine, sphingomyelin and phosphatidyl ethanolamine.

In addition, other lipids, such as cholesterol and analogs thereof and diacetylphosphate can be included in the lipid bilayer so as to stabilize the ganglioside liposomes.

The above-described liposome components can be employed alone or in combination in the ganglioside liposomes of the present invention.

The amount of phospholipids employed in the ganglioside liposomes is not critical to the present invention. Generally, the phospholipids comprise about 50 to 60% by weight of the ganglioside liposomes of the present invention.

The amount of other lipids employed in the ganglioside liposomes is not critical to the present invention. Generally, the other lipids comprise about 25 to 30% by weight of the ganglioside liposomes of the present invention.

The particular ganglioside employed in the present invention is not critical thereto. Examples of such gangliosides include polysialyl gangliosides, such as $GT_{1b}$, $GT_{1b}$ and $GQ_1$ (Hakomori, S., *Handbook of Lipid Research*, Vol. 3, "Shingolipid Biochemistry", Eds. Kanfer, J. N. et al, Plenum Press, New York, pages 1–165 (1983); and Svennerholm, L., *J. Lipid Res.*, 5:145 (1964) and high density monosialyl gangliosides such as $GM_3$, $GM_{1a}$ and $LM_1$ (Hakomori. S., *Handbook of Lipid Research*, Vol. 3, "Shingolipid Biochemistry", Eds. Kanfer, J. N. et al, Plenum Press, New York, pages 1–165 (1983)).

Polysialyl gangliosides are preferably employed in the present invention since the presence of the polysialyl Glc greatly increases the negative charge of the ganglioside liposomes. This is believed to inhibit the interaction of the ganglioside liposomes with macrophages and reticuloendothelial system cells. That is, inclusion of polysialyl gangliosides in the ganglioside liposomes not only offers a convenient structure for conjugating to the tumor-associated antibody but, also, the highly negative polysialyl Glc avoids undesirable interaction of the ganglioside liposome with macrophages and reticuloendothelial system cells.

The above-described gangliosides can be employed alone or in combination in the ganglioside liposomes of the present invention.

The amount of ganglioside which is contained in the ganglioside liposomes is an amount sufficient to prevent interaction with the reticuloendothelial system and/or to anchor the tumor-associated antibody or ligand. Generally, the amount of ganglioside contained in the ganglioside liposomes is about 10 to 20% by weight of the ganglioside liposomes of the present invention.

The particular differentiation-inducer employed in the present invention is not critical thereto. Examples of such differentiation-inducers include n-butyric acid or a salt thereof: dimethyl sulfoxide (DMSO); 12-O-tetradecanoyl phorbol-13-acetate (TPA); dihydroteleocidin B: teleocidin B: teleocidin A; and retinoic acid.

The above-described differentiation-inducers can be employed alone or in combination in the microspheres of the present invention.

The amount of differentiation-inducer which is contained in the microspheres, preferably in the ganglioside liposomes, is an amount sufficient to induce tumor differentiation and the amount varies depending upon the specific differentiation-inducer employed and the tumor to be treated. Generally, the amount of differentiation-inducer contained in the microspheres, preferably in the ganglioside liposomes, is about 2.0 to 20 mg/mg of tumor-associated antibody or ligand conjugated to the microsphere, preferably about 10 to 20 mg/mg of tumor-associated antibody or ligand conjugated to the microsphere, more preferably about 15 to 18 mg/mg of tumor-associated antibody or ligand conjugated to the microsphere.

The differentiation-inducer is contained in the microspheres in the form of an aqueous solution thereof. The solution is prepared by dissolving or dispersing the differentiation-inducer in a solvent such as physiological buffered saline. Ringer-Tyrode solution or Ringer-Locke solution, which are physiological buffered salines containing KCl, $CaCl_2$, $NaHCO_3$ and glucose, or Kreb's-Ringer solution, which is a physiologically buffered saline containing KCl, $CaCl_2$, $MgSO_4$ and phosphate carbonate. If desired, a mixture of vitamins and/or amino acids can be added to these solutions.

The method for preparing synthetic microspheres containing a differentiation-inducer therein is not critical to the present invention. Methods for preparing synthetic microspheres containing a differentiation-inducer therein which can be employed in the present invention include, for example, those described in Betts, L. R. et al, *Fertil. Steril.*, 31:545-551 (1979); and *Microspheres and Drug Therapy*, Eds. Davis, S. S. et al, Elsevier, New York (1984). Briefly, the copolymer forming the synthetic microspheres is mixed with a solvent and differentiation-inducer. Then, the solvent is evaporated which gives rise to the formation of synthetic microspheres containing a differentiation-inducer therein.

The method for preparing the ganglioside liposomes containing a differentiation-inducer therein is not critical to the present invention. Methods for preparing the ganglioside liposomes containing a differentiation-inducer therein which can be employed in the present invention include, for example, those described in Jonathan, S. M. et al, Biochem. Biophys. Acta, 193:82-91 (1969) or Batzri, S. et al, *Biochem. Biophys. Acta*, 298:1015-1019 (1973). Briefly, the lipid components and ganglioside are dissolved in a chloroform-methanol solvent system (2:1 (v/v)) to dryness under a nitrogen stream. The dried residue is then sonicated in physiological buffered saline containing a differentiation-inducer therein for 2 to 3 hours or dissolved in ethanol or tetrahydrafuran and injected into the physiological buffered saline containing a differentiation-inducer therein. The resulting ganglioside liposome containing a differentiation-inducer therein can be purified by gel filtration on Sepharose 4B as described by, for example, Urdal, D. L. et al, *J. Biol. Chem.*, 255:10509-10516 (1980). Alternatively, the method described in Example 1 below can be employed for preparing the ganglioside liposomes containing a differentiation-inducer therein.

The particular tumor-associated antibody employed in the present invention is not critical thereto. Examples of such tumor-associated antibodies include SH1 antibody, an $IgG_3$ anti-$Le^x$ antibody prepared by immunizing mice with $Le^x$ glycolipid on Salmonella minnesotae as described by Young. W. W. et al, *J. Exp. Med.*, 150:1008-1019 (1979); anti-$GD_3$, which is specific for melanomas: anti-sialyldifucosyl type 2 chain (FH6), which is specific for colorectal carcinoma; anti-$Le^Y$, which is specific for gastrointestinal cancer; and anti-sialyl-Tn, which is specific for various types of human epithelial cancer including lung, breast and colonic cancers (Hakomori, S. et al, *Natl. Cancer Inst.*, 71:231-251 (1983); Hakomori, S. *Ann. Rev. Immunol.*, 2:103-126 (1984): and Hakomori, S. et al, *In: Monoclonal Antibodies and Functional Cell Lines*, Eds. R. H. Kennett et al, Plenum Press, New York, pages 67-100 (1984)).

The above-described tumor-associated antibodies can be employed alone or in combination when conjugated to the microspheres of the present invention.

The particular tumor-associated ligand employed in the present invention is not critical thereto. Examples of such tumor-associated ligands include:

(1) classical lectins, such as peanut lectin (*Arachis hypogaea*) and snail lectin (*Helix pomatia*), which are not highly specific to tumor cells;

(2) tumor-associated lectins, most of which are directed to $\beta$-galactosyl residues (Gabius H. J. et al, *Cancer Lett.*, 31:139-145 (1986): and Gabius. H. J. et al, *Cancer Res.*, 45:283-287 (1985)). $\beta$-galactosyl structures linked to differentiation-inducers or to differentiation-inducer containing microspheres can be useful ligands for targeting differentiation-inducers to tumor cells which contain lectins directed to $\beta$-galactosyl residues. Through systemic analysis of various tumor-associated lectins, other carbohydrate structures linked to differentiation-inducers should also be useful for the targeting of differentiation-inducers to tumor cells;

(3) hormones, some tumor cells. e.g., some breast cancers and essentially all malignant chorionic epitheliomas, are dependent on the female hormone estrogen. Prostate cancers are sensitive to either estrogens or androgens. Differentiation-inducers coupled to such hormones can be targeted to specific types of hormone-dependent tumor cells: and (4) factors essential for active proliferation of tumor cells. e.g., transferrin and tumor cell growth factors $\alpha$ and $\beta$.

The above-described tumor-associated ligands can be employed alone or in combination when conjugated to the microspheres of the present invention.

The amount of tumor-associated antibody or ligand conjugated to the microspheres, preferably ganglioside liposomes, containing a differentiation-inducer therein is not critical to the present invention. Generally, the amount of tumor-associated antibody or ligand conjugated to the microspheres containing a differentiation-inducer therein is about 1.0 to 5.0 $\mu g/\mu mole$ of microsphere, preferably about 2.0 to 5.0 $\mu g/\mu mole$ of microsphere.

Synthetic microspheres containing differentiation-inducers therein can be conjugated to tumor-associated antibodies or ligands as described in *Microspheres in Drug Therapy*, Eds. Davis, S. S. et al. Elsevier, New York (1984). Briefly, the synthetic microspheres and tumor-associated antibodies or ligands are mixed in an appropriate buffer and due to the hydrophobicity of the surface of the synthetic microspheres, the tumor-associated antibodies or ligands adhere thereto. Alternatively, synthetic microspheres containing an aldehyde group can be coupled to the tumor-associated antibodies or ligands by reductive amination with cyanoborohydride in the same manner discussed below as the tumor-associated antibodies or ligands are coupled to the periodate-oxidized ganglioside liposome. In addition, synthetic microspheres containing an azide group can be coupled to the carboxyl group of tumor-associated antibodies or ligands. Further, synthetic microspheres containing a carboxy N-succinimide group can be coupled to the amino group of tumor-associated antibodies or ligands.

The method of coupling the tumor-associated antibody to the ganglioside liposomes containing a differentiation-inducer therein is not critical to the present invention. For example: (i) the ganglioside liposome can be coupled to the amino group of the tumor-associated antibody by oxidation of the sialic acid moiety of the ganglioside with sodium metaperiodate followed by treating the tumor-associated antibody with sodium borohydride; (ii) the ganglioside liposome can be coupled to the tumor-associated antibody by the use of carbodiimide, which links the amino group of phosphatidylcholine with the carboxyl group of the tumor-associated antibody; and (iii) the ganglioside liposome can be coupled to the tumor-associated antibody by the use of N-hydroxysuccinimidyl-3-(2-pyridyldithio)-propinate (SPDP), which produces a thioether bridge between the amino group of phosphatidylcholine and the carboxyl group of the tumor-associated antibody.

In the present invention, the conjugation of the tumor-associated antibody or ligand to the ganglioside liposome does not necessarily involve the ganglioside. That is, phosphatidyl ethanolamine can be modified to biotinylphosphatidyl ethanolamine and incorporated into the ganglioside liposome. The biotinyl group can then be coupled to the tumor-associated antibody or ligand through avidin as described by Urdal, D. L. et al, *J. Biol. Chem.*, 255:10509–10516 (1980). Other well known methods for conjugating proteins to liposomes, for example as described in Leserman, L. D., Liposomes, *Drugs and Immunocompetent Cell Functions*, Eds. Nicholau, C. et al. Academic Press, New York, pages 109–122 (1981) and Machy, P. et al, *In: Liposomes in Cell Biology and Pharmacology*, John Libbey & Co., London, pages 100–153 (1987), can also be employed in the present invention. However, the coupling of the tumor-associated antibody or ligand to the ganglioside in the ganglioside liposome is preferred since the ganglioside is a naturally occurring substance and prevents undesirable interaction of the ganglioside liposome with macrophages and reticuloendothelial system cells.

In still another embodiment, the above-described objects of the present invention have been met by a method for treating a tumor comprising administering to a subject afflicted with a tumor, a pharmaceutically effective amount of a tumor-associated antibody or ligand conjugated to a synthetic or natural microsphere, preferably a ganglioside liposome, wherein said microsphere contains a differentiation-inducer therein.

The pharmaceutically effective amount of the above-described conjugates containing a differentiation-inducer therein to be administered will vary depending upon the age, weight, sex and species of the subject to be administered, the amount of differentiation-inducer contained in the microspheres, the activity of the differentiation-inducer, the binding affinity of the tumor-associated antibody or ligand and the amount of tumors in the subject. Generally, the pharmaceutically effective amount to be administered is about 0.3 to 1.0 mg/kg of body weight, preferably about 0.5 to 1.0 mg/kg of body weight.

The above-described conjugates containing a differentiation-inducer therein are diluted prior to administration. For dilution, a pharmaceutically acceptable diluent can be employed. The particular pharmaceutically acceptable diluent employed is not critical to the present invention. Examples of such pharmaceutically acceptable diluents include physiological buffered saline, Ringer's solution, vitamin cocktail and amino acid vitamin cocktail.

The above-described conjugates containing a differentiation-inducer therein can be administered to a subject possessing a tumor using a variety of modes of administration depending on the situation. Examples of such modes of administration include intravenous administration for essentially all kinds of cancers, intraperitoneal administration for ovarian and gastrointestinal cancers, and intra-arterial administration during surgical treatment.

The particular tumor-associated antibody or ligand conjugated microsphere containing a differentiation-inducer therein that is administered will depend upon the particular tumor that is to be treated. That is, the particular tumor-associated antibody or ligand chosen to be conjugated to the microsphere containing a differentiation-inducer therein is one which is specific for the tumor to be treated.

Furthermore, the particular differentiation-inducer chosen to be contained in the microsphere is one which has a strong differentiation-inducing effect on the tumor to be treated.

There are no specific parameters for choosing the specific phospholipids to employ in the ganglioside liposomes of the present invention. It is preferable to use synthetic phospholipids such as dipalmitoyl phosphatidylcholine rather than natural phospholipids, because the synthetic forms have constant compositions, properties and availability.

In addition, there are no specific parameters for choosing the specific ganglioside to employ in the ganglioside liposomes. Any ganglioside is acceptable for the purpose of coupling the tumor-associated antibody or ligand. However, in order to achieve a high density negative charge on the ganglioside liposomes, polysialyl gangliosides are preferred.

In another embodiment, the above-described objects of the present invention have been met by a tumor-associated antibody or ligand conjugated to a differentiation-inducer.

The particular amount of differentiation-inducer to be conjugated to the tumor-associated antibody or ligand is not critical to the present invention. Generally, the amount of differentiation-inducer conjugated to the tumor-associated antibody or ligand should be the maximal amount allowable without decreasing the tumor-associated antibody or ligand binding activity. Generally, about 1.0 to 10 moles of differentiation-inducer is conjugated to 1.0 mole of tumor-associated antibody or ligand.

Each differentiation-inducer requires a different method of coupling to the tumor-associated antibody or ligand since each differentiation-inducer has a different functional group. Methods for covalent coupling of differentiation-inducers to carboxyl, amino, azido or aldehyde groups are well known in the art. For example, n-butyric acid can be coupled to an amino group of the tumor-associated antibody or ligand using the carbodiimide method. A number of carbodiimide reagents are readily available for this purpose. e.g., 1-ethyl-3-(3-dimethylaminopropyl) carbodiimide hydrochloride (EDC) and N-hydroxysulfosuccinimide (sulfo-NHS) (Staros, J. V. et al, *Anal. Biochem.*, 156:220–222 (1986)). If the differentiation-inducer contains an -SH group, N-succinimidyl 3-(2-pyridyldithio)propionate (SPDP)

can be employed (Carlsson, J. et al, *Biochem. J.*, 173:723–737 (1978)).

In another embodiment, the above-described objects of the present invention have been met by a method for treating a tumor comprising administering to a subject afflicted with a tumor, a pharmaceutically effective amount of a tumor-associated antibody or ligand conjugated to a differentiation-inducer.

The pharmaceutically effective amount of the tumor-associated antibody or ligand conjugated to a differentiation-inducer to be administered will vary depending upon the age, weight, sex and species of the subject to be administered, the amount of differentiation-inducer contained in the conjugate, the activity of the differentiation-inducer, the binding affinity of the tumor-associated antibody or ligand and the amount of tumors in the subject. Generally, the pharmaceutically effective amount to be administered is about 0.1 to 1.0 mg/kg of body weight, preferably about 0.5 to 1.0 mg/kg of body weight.

The tumor-associated antibody or ligand conjugated to a differentiation-inducer is diluted prior to administration. For dilution, a pharmaceutically acceptable diluent can be employed. The particular pharmaceutically acceptable diluent employed is not critical to the present invention. Examples of such pharmaceutically acceptable diluents include physiological buffered saline, Ringer's solution, vitamin cocktail and amino acid vitamin cocktail.

The tumor-associated antibody or ligand conjugated to a differentiation-inducer can be administered to a subject possessing a tumor using a variety of modes of administration depending on the situation. Examples of such modes of administration include intravenous administration for essentially all kinds of cancers, intraperitoneal administration for ovarian and gastrointestinal cancers, and intra-arterial administration during surgical treatment.

The particular tumor-associated antibody or ligand conjugated to the differentiation-inducer will depend upon the particular tumor that is to be treated. That is, the particular tumor-associated antibody or ligand conjugated to the differentiation-inducer is one which is specific for the tumor to be treated. Further, the particular differentiation-inducer conjugated to the tumor-associated antibody or ligand is one which has a strong differentiation-inducing effect on the tumor to be treated.

The following examples are provided for illustrative purposes only and are in no way intended to limit the scope of the present invention.

EXAMPLE 1

Preparation of Anti-Le$^x$ Antibody-Conjugated GM$_3$ Ganglioside Liposome Containing n-Butyric Acid While this example describes the use of phosphatidylcholine and cholesterol as the primary lipid components, GM$_3$ ganglioside as the ganglioside, n-butyric acid as the differentiation-inducer, and SH1 antibody as the tumor-associated antibody, other primary lipid components, such as those described above, other gangliosides, such as those described above, other differentiation-inducers, such as those described above and other tumor-associated antibodies or ligands, such as those described above, could also be employed using the procedures of this example to prepare other tumor-associated antibody (ligand)-conjugated ganglioside liposomes containing a differentiation-inducer therein without departing from the spirit and scope of the present invention.

Phosphatidylcholine (a synthetic dipalmitoyl derivative), cholesterol and GM$_3$ ganglioside, in a molar ratio of 1:0.75:0.1 or 1:0.5:0.05, and n-butyric acid, in an amount of 1.0 g/10 μmol of phosphatidylcholine, were dissolved in a chloroform-methanol solvent system (2:1 (v/v)). The solution was mixed well at 25° C. and dried at 30° C. under an N$_2$ stream. Then, 1.0 ml of 0.5M phosphate buffered saline (pH 6.5) was added per 10 μmol of phosphatidylcholine. (It should be noted that the particular buffer and pH employed are not critical to the present invention.) Next, sonication was carried out for 3 to 5 hours in a Branson Model 5200 sonicator. Sonication was performed at room temperature and the temperature rose slowly during sonication and reached approximately 40° C. after 1 hour. Sonication was carried out in order to convert the solid-phase phospholipid/cholesterol/ganglioside mixture into a ganglioside liposome. The resulting sonicate was dialyzed against 1.0 liters of 0.05M phosphate buffered saline (pH 6.5) overnight to remove excess differentiation-inducer, i.e., n-butyric acid.

The gangliosides in the resulting ganglioside liposomes containing n-butyric acid therein were oxidized in 8.0 mM sodium metaperiodate for 2 hours at room temperature in the dark so as to convert the C7 primary hydroxy group of sialic acid in the ganglioside to a C7 aldehyde group which is susceptible to subsequent aminaton with the tumor-associated antibody and does not alter the carboxyl negative charge of the sialic acid residue, which is the essential group of the ganglioside preventing interaction with macrophages and reticuloendothelial system cells. The resulting oxidized ganglioside liposomes containing n-butyric acid were then dialyzed against 2.0 liters of phosphate buffered saline (pH 6.5) overnight to remove excess sodium metaperiodate.

10 μmol of the resulting ganglioside liposomes containing n-butyric acid therein were coupled to 10 mg of SH1 antibody, an IgG$_3$ anti-Le$^x$ antibody, by the addition of 1.6 μmole of sodium cyanoborohydride in 0.05M phosphate buffered saline (pH 6.5) and incubating for 18 hours at room temperature. Then, the reaction mixture was separated at 4° C. on a Sepharose 4B column (Sigma Chemical Co.) which had been previously equilibrated in 0.05M phosphate buffered saline (pH 7.4). The antibody-conjugated ganglioside liposomes containing n-butyric acid therein were eluted with the same buffer in a void volume of about 50 ml. Approximately 1.0 mg of SH1 antibody conjugated to 10 μmol of ganglioside liposomes containing n-butyric acid therein was obtained using this procedure.

EXAMPLE 2

In Vitro Targeting of HRT-18 Cells

Figure 1:
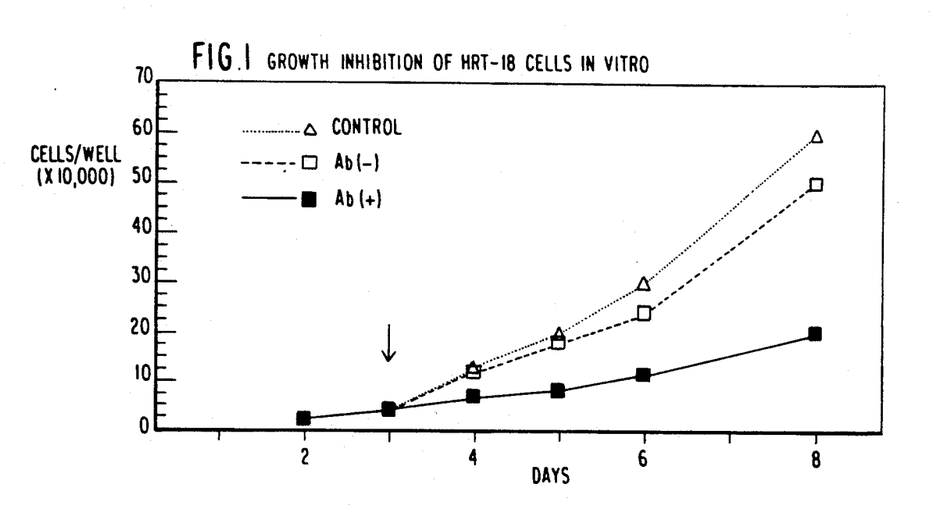
FIG. 1 illustrates the in vitro growth inhibition of human colonic carcinoma HRT-18 cells, which highly express Le$^x$ antigen, using SH1 antibody coupled to ganglioside liposomes, wherein the ganglioside liposomes contain n-butyric acid therein.

HRT-18 cells were cultured at 37° C. in DMEM medium (Gibco) supplemented with 10% (v/v) heat-inactivated fetal calf serum. The cells were seeded in 96-well Falcon trays in an amount of 2,000 cells/well. Then, either: (i) 10 μl of a liposome suspension containing 0.5 μmol of n-butyric acid therein per 0.03 μmol of liposome, prepared as described in Example 1 but omitting the ganglioside; (ii) 10 μl of the antibody-conjugated ganglioside liposome containing n-butyric acid therein prepared as described in Example 1; or (iii) 10 μl of physiological buffered saline, were added to the wells. The effect of these additions on in vitro growth inhibition of HRT-18 cells is shown in FIG. 1. Specifically, FIG. 1 shows the increase in the number of HRT-18 cells cultured in vitro in DMEM medium supplemented with 10% (v/v) heat-inactivated fetal calf serum containing anti-Le$^x$ antibody-conjugated ganglioside liposomes containing n-butyric acid therein (solid line with closed circles) compared with the same medium containing liposomes containing n-butyric acid therein which are not conjugated to anti-Le$^x$ antibody (dashed line with open squares). The control growth curve (dotted line with open triangles) represents cells grown in the same medium without liposomes.

As shown in FIG. 1, the antibody-conjugated ganglioside liposomes containing n-butyric acid therein of the present invention were effective in inhibiting the growth of HRT-18 cells in vitro.

Furthermore, HRT-18 cells treated with the antibody-conjugated ganglioside liposomes containing n-butyric acid therein underwent morphological changes. i.e., the cells were flattened and discrete in their boundaries and cell growth behavior came to resemble that of normal cells. i.e., cell growth was contact-inhibited.

EXAMPLE 3

In Vivo Targeting of HT-29 and HRT-18 Tumors

A. Accumulation of Liposomes

Nude mice were inoculated subcutaneously with 5×106 HT-29 cells (ATCC No. HTB-38)/animal. When tumors grew to 0.5 to 1.0 cm in diameter about 14 days, the mice were injected intravenously with either: (i) 0.2 ml/mouse of the liposome suspension prepared as described in Example 2; or (ii) 0.2 ml/mouse of the antibody-conjugated ganglioside liposomes containing n-butyric acid therein prepared as described in Example 1. Both the liposome suspension and the antibody-conjugated ganglioside liposomes containing n-butyric acid therein were previously labelled with $^{14}$C-cholesterol by substituting $^{14}$C-cholesterol (Dupont, Boston, Mass.) for cholesterol in the preparation thereof.

The mice were sacrificed 6, 12, 24 and 48 hours after injection of the liposome suspension or the antibody-conjugated ganglioside liposomes containing n-butyric acid therein. Liposome accumulation was assessed in the tumor, the kidney, the liver, the spleen and the lung of each mouse using the following formula:

$$\% \text{ accumulation} = \frac{\text{cpm/weight (tissue)}}{\text{cpm/weight (total)}}$$

The results are shown in FIGS. 2A to 2E.

Figure 2A:
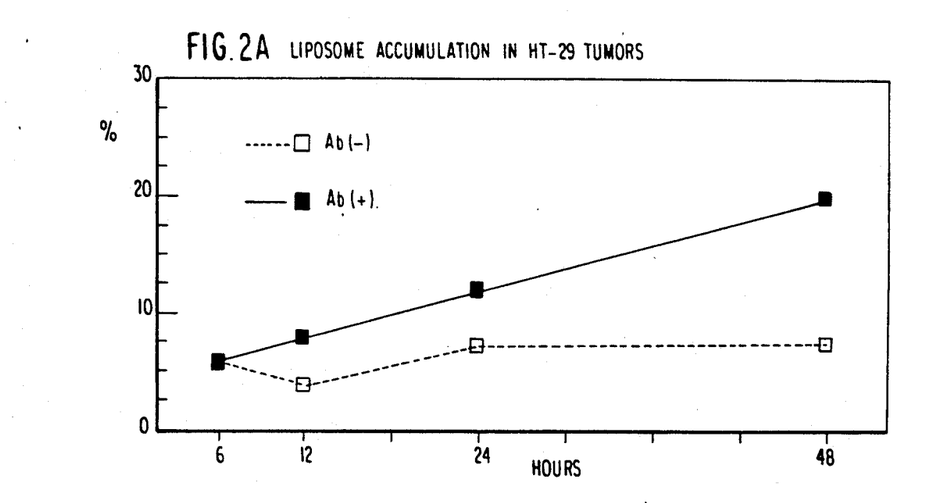
FIG. 2A illustrates the accumulation levels, in human colonic carcinoma HT-29 tumors in mice, of SH1 antibody coupled to ganglioside liposomes, wherein the ganglioside liposomes contain n-butyric acid therein.
Figure 2B:
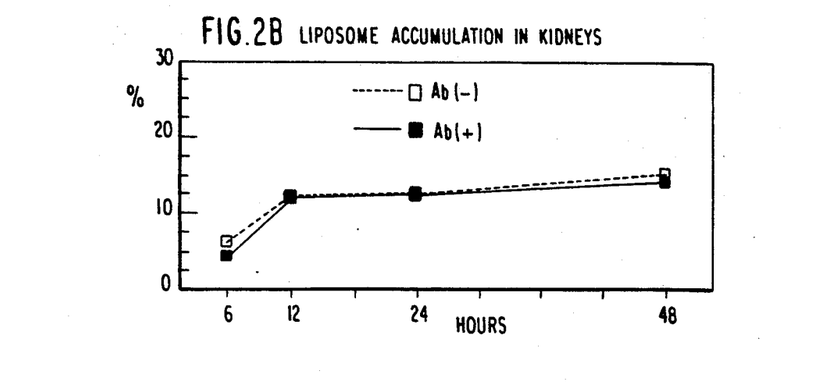
FIG. 2B illustrates the accumulation levels, in mice kidneys, of SH1 antibody coupled to ganglioside liposomes, wherein the ganglioside liposomes contain n-butyric acid therein.
Figure 2C:
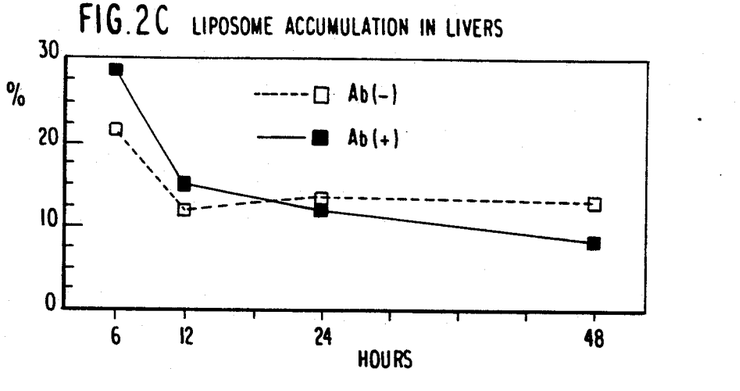
FIG. 2C illustrates the accumulation levels, in mice livers, of SH1 antibody coupled to ganglioside liposomes, wherein the ganglioside liposomes contain n-butyric acid therein.
Figure 2D:
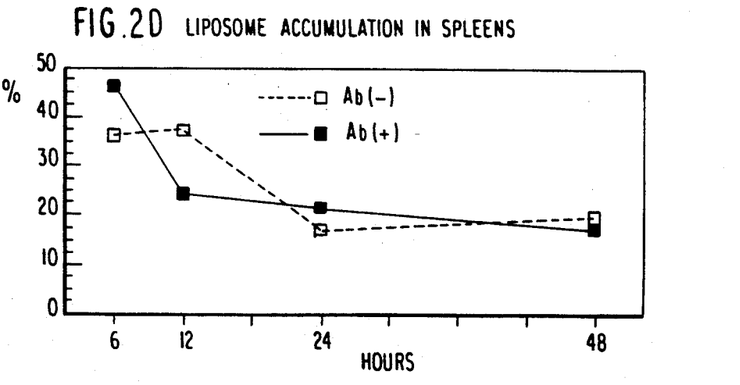
FIG. 2D illustrates the accumulation levels, in mice spleens, of SH1 antibody coupled to ganglioside liposomes, wherein the ganglioside liposomes contain n-butyric acid therein.
Figure 2E:
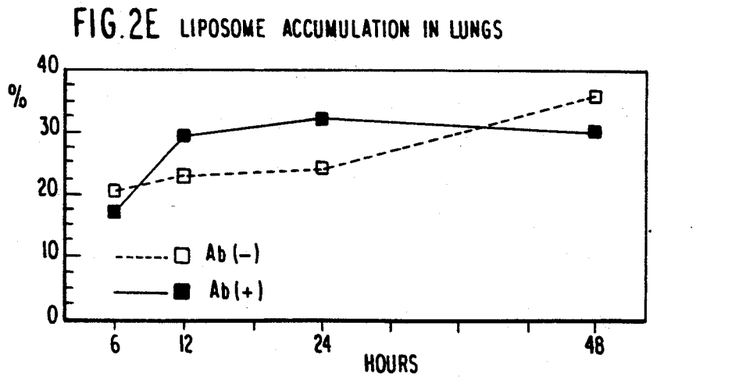
FIG. 2E illustrates the accumulation levels, in mice lungs, of SH1 antibody coupled to ganglioside liposomes, wherein the ganglioside liposomes contain n-butyric acid therein.

As shown in FIG. 2A, only the accumulation of antibody-conjugated ganglioside liposomes containing n-butyric acid therein (solid line with closed circles) in HT-29 tumors increased as a function of time. On the other hand, as shown in FIGS. 2B and 2E. although there was accumulation of both the liposome suspension and the antibody-conjugated ganglioside liposomes containing n-butyric acid therein in the kidneys and the lungs of the mice as a function of time, no difference was observed between the accumulation of the liposome suspension and the accumulation of the antibody-conjugated ganglioside liposomes containing n-butyric acid therein. Further, as shown in FIGS. 2C and 2D. there was essentially no accumulation of either the liposome suspension or the antibody-conjugated liposome containing n-butyric acid therein in the livers or the spleens of the mice as a function of time. This demonstrates that accumulation of antibody-conjugated ganglioside liposomes in kidneys, livers, spleens and lungs does not depend upon the antibody. i.e., there is non-specific deposition rather than specific targeting. In striking contrast, accumulation of ganglioside liposomes in HT-29 tumors is clearly dependent on the presence of the conjugated antibody.

B. Inhibition of HT-29 or HRT-18 Tumor Growth In Vivo

Nude mice were inoculated subcutaneously with 5×106 HT-29 cells or HRT-18 cells/animal. When tumors grew to 0.3 to 0.5 cm in diameters, about 5 to 10 days, the mice were injected intravenously with either: (i) 0.2 ml/mouse of the liposome suspension prepared as described in Example 2; (ii) 0.2 ml/mouse of the antibody-conjugated ganglioside liposomes containing n-butyric acid therein prepared as described in Example 1; or (iii) 0.2 ml/mouse of physiological buffered saline every 5 days. The dates of injection are indicated by arrows on the upper margin of FIGS. 3 and 4. Tumor weight was estimated as follows:

Tumor weight (mg) = 0.5 × length (mm) × width$^2$ (mm$^2$)

Figure 3:
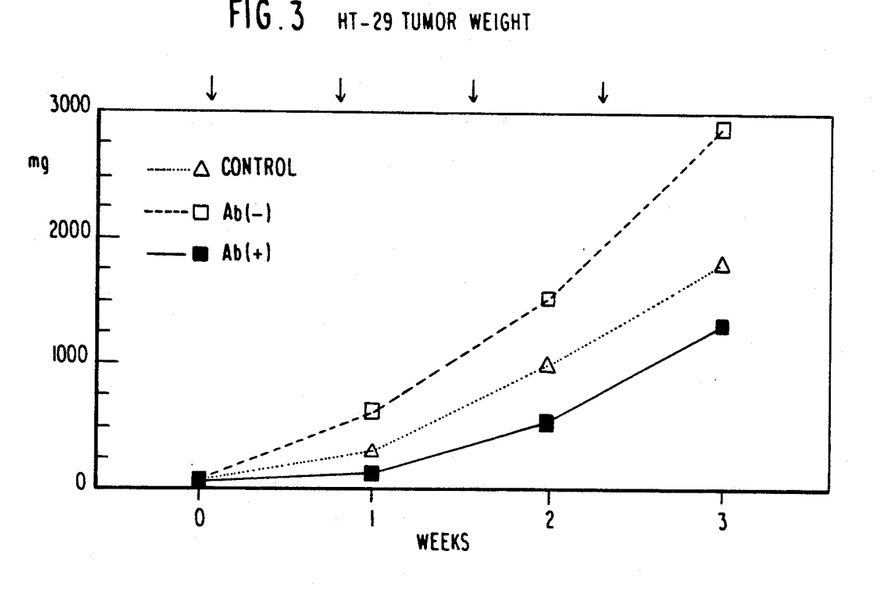
FIG. 3 illustrates the in vivo growth inhibition of human colonic carcinoma HT-29 tumors using SH1 antibody coupled to ganglioside liposomes, wherein the ganglioside liposomes contain n-butyric acid therein.
Figure 4:
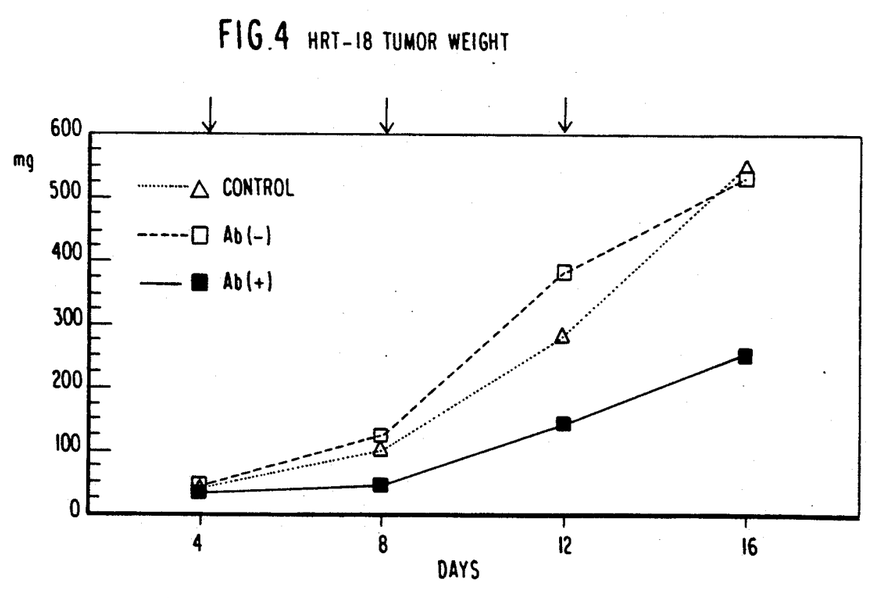
FIG. 4 illustrates the in vivo growth inhibition of human colonic carcinoma HRT-18 tumors using SH1 antibody coupled to ganglioside liposomes, wherein the ganglioside liposomes contain n-butyric acid therein.

The results are shown in FIGS. 3 and 4.

As shown in FIGS. 3 and 4, tumor growth was clearly inhibited in animals injected with the antibody-conjugated ganglioside liposomes containing n-butyric acid therein (solid line with closed circles) in comparison to untreated controls (dotted line with open triangles) or animals injected with the liposome suspension. i.e., unconjugated liposomes (dotted line with open squares). These results demonstrate specific inhibition of tumor growth by administration of anti-Le$^x$ conjugated liposomes containing n-butyric acid therein.

EXAMPLE 4

Preparation of Anti-Le$^x$ Antibody-Conjugated Synthetic Microspheres Containing n-Butyric Acid While this example describes the use of synthetic microspheres derived from lactide glycolide copolymers or polyacrolein graft copolymers, n-butyric acid as a differentiation-inducer and SH1 antibody is a tumor-associated antibody, other synthetic microspheres, such as those described above, other differentiation-inducers, such as those described above, and other tumor-associated antibodies or ligands, such as those described above, could also be employed using the procedures of this example to prepare other tumor-associated antibody (ligand)-conjugated synthetic microspheres containing differentiation-inducers therein without departing from the spirit and scope of the present invention.

An organic solution comprising 20 ml of methylene chloride. 927 mg of lactide glycolide copolymer and about 250 mg to 1.0 g of n-butyric acid is rapidly poured into 250 ml of water containing 0.27 wt % of polyvinyl alcohol. Then, the methylene chloride is evaporated at 22° C. to prepare synthetic microspheres containing n-butyric acid therein. The resulting synthetic microspheres containing n-butyric acid therein are then incubated with 10 mg of SH1 antibody for 24 hr in 0.05M phosphate buffered saline (pH 7.4). The tumor-associated antibody is conjugated to the synthetic microsphere surface due to the hydrophobicity of the synthetic microsphere surface. Next, the resulting mixture is applied on a Sepharose 4B column which has been previously equilibrated in 0.05M phosphate buffered saline (pH 7.4) to separate the tumor-associated antibody-conjugated synthetic microspheres from free tumor-associated antibodies.

Alternatively, synthetic microspheres can be formed from polyacrolein graft copolymers by catalytic reaction using. e.g., UV irradiation as a catalyst. For example. 0.1 g of polystyrene. 4.0 ml of a 0.4% (w/v) polyethylene oxide solution in water, 2.0 ml of a 20% (w/v) acrolein solution in water and 0.01 mg of SDS are mixed together. Nitrogen gas is bubbled into the solution for 10 min to remove dissolved oxygen prior to initiation of polymerization. The solution is irradiated for 7 hours using a cobalt gamma-radiation source at a dosage of 0.12 Mrad/hr. After irradiation, the synthetic microspheres formed are separated by centrifugation and differentiation-inducers can be encapsulated therein by dissolving differentiation-inducers in an aqueous solution When these synthetic microspheres are employed, the binding of the tumor-associated antibody thereto is carried out in 0.1M phosphate buffered saline (pH 5.2). More specifically. 2.0 mg of the synthetic microspheres containing n-butyric acid therein are mixed with 5.0 g of SH1 antibody. The reaction mixture is sonicated for 30 seconds and then rotated overnight at room temperature. After conjugation, the reaction mixture is centrifuged. The synthetic microspheres are resuspended in 1.0 ml of a solution comprising 1.0M ethanolamine and 0.1% (v/v) Tween 20 (pH 9.5) and rotated for 3 hours to block the remaining reactive groups. The tumor-associated antibody-conjugated synthetic microspheres are then washed extensively with phosphate buffered saline (pH 7.4).

EXAMPLE 5

Preparation of Anti-Le$^x$ Antibody-Conjugated n-Butyric Acid

While this example describes the use of n-butyric acid as the differentiation-inducer and SH1 antibody as the tumor-associated antibody, other differentiation-inducers, such as those described above, and other tumor-associated antibodies or ligands, such as those described above, could also be employed using procedures of this example to prepare other tumor-associated antibody (ligand)-conjugated differentiation-inducers without departing from the spirit and the scope of the present invention.

Carbodiimide was added to an aqueous solution comprising 10 mg of SH1 antibody. 0.1 mg of n-butyric acid and 5.0 mM N-hydroxysulfosuccinimide (a catalyst which reacts with peptide carboxyl groups to form active esters which readily react with primary amines). to a total concentration of 0.1M. The pH of the reaction mixture was adjusted to pH 7.4 with phosphate buffered saline (pH 8.0) and incubated overnight at room temperature. The resulting anti-Le$^x$ antibody-conjugated n-butyric acid was separated from unreacted components at 4° C. on a Sephadex G-100 column (Sigma Chemical Co.) which had been previously equilibrated in 0.05M phosphate buffered saline (pH 7.4). The anti-Le$^x$ antibody-conjugated n-butyric acid was eluted with the same buffer in a 2.0 to 6.0 ml elution volume. Approximately 2.0 mg of anti-Le$^x$ antibody was conjugated to 10 μg of n-butyric acid using this procedure.

While the invention has been described in detail and with reference to specific embodiments thereof, it will be apparent to one skilled in the art that various changes and modifications can be made therein without departing from the spirit and scope thereof.

We claim:

1. A method for treating a tumor comprising administering to a subject afflicted with said tumor, a differentiation inducing effective amount of a composition comprising an antibody directed to said tumor, wherein said antibody is conjugated to a ganglioside liposome comprising a phospholipid, or a non-antibody ligand directed to said tumor, wherein said ligand is conjugated to a ganglioside liposome comprising a phospholipid, wherein said ganglioside liposome contains in the core thereof a differentiation-inducer selected from the group consisting of n-butyric acid or a salt thereof and retinoic acid.

2. The method as claimed in claim 1, wherein said ganglioside liposome comprises as a main component, a phospholipid selected from at least one member of the group consisting of dipalmitoyl phosphatidylcholine, distearyl phosphatidyl choline, sphingomyelin and phosphatidyl ethanolamine.

3. The method as claimed in claim 1, wherein said ganglioside in said ganglioside liposome is selected from at least one member of the group consisting of a polysialyl ganglioside selected from at least one member of the group consisting of $GT_{1b}$, $GT_{1a}$ and $GQ_1$ and a high density monosialyl ganglioside selected from at least one member of the group consisting of $GM_3$, $GM_{1a}$ and $LM_1$.

4. The method as claimed in claim 1, wherein said pharmaceutically effective amount is about 0.3 to 1.0 mg/kg of body weight.

5. The method as claimed in claim 4, wherein said pharmaceutically effective amount is about 0.5 to 1.0 mg/kg of body weight.

6. The method as claimed in claim 1, wherein said antibody directed to a tumor or said ligand directed to a tumor is administered intravenously, intraperitoneally or intra-arterially.

* * * * *